(12) United States Patent
Wang et al.

(10) Patent No.: US 8,119,416 B2
(45) Date of Patent: Feb. 21, 2012

(54) MALDI ANALYSIS USING MODIFIED MATRICES WITH AFFINITY GROUPS FOR NON-COVALENT BINDING WITH ANALYTES

(75) Inventors: Tianxin Wang, Boyds, MD (US); Qun Liu, Boyds, MD (US); Sha Zhou Zou, Columbia, MD (US)

(73) Assignee: Wuxi WeiYi Zhinengkeji, Inc., Wuxi, JiangSu (CN)

( * ) Notice: Subject to any disclaimer, the term of this patent is extended or adjusted under 35 U.S.C. 154(b) by 13 days.

(21) Appl. No.: 12/456,786

(22) Filed: Jun. 23, 2009

(65) Prior Publication Data

US 2009/0269855 A1    Oct. 29, 2009

Related U.S. Application Data

(63) Continuation-in-part of application No. 10/755,986, filed on Jan. 13, 2004, now Pat. No. 7,550,301.

(51) Int. Cl.
*G01N 24/00* (2006.01)

(52) U.S. Cl. ......... 436/173; 250/281; 250/282; 250/288

(58) Field of Classification Search ..................... None
See application file for complete search history.

(56) References Cited

U.S. PATENT DOCUMENTS

| 5,719,060 | A | 2/1998 | Hutchens et al. |
| 5,952,654 | A | 9/1999 | Giese |
| 6,093,541 | A | 7/2000 | Nelson |
| 6,316,266 | B1 | 11/2001 | Nelson |

OTHER PUBLICATIONS

T. William Hutchens and Tai-Tung Yip, "New Desorption Strategies for the Mass Spectrometric Analysis of Macromolecules", Rapid Communic. Mass Spectrom., 1993, v. 7, pp. 576-580.*
U.S. Appl. No. 10/755,986, filed Jul. 22, 2004, Tianxin Wang.

* cited by examiner

*Primary Examiner* — Yelena G Gakh

(57) ABSTRACT

Methods and compounds are provided to improve the desorption and ionization of analyte for mass spectrometry analysis. More specifically, it is for laser desorption/ionization mass spectrometry. The method uses photon energy absorbing molecules that can bind with analyte either temporarily or permanently to improve the desorption and ionization of analyte. The photon energy absorbing molecules can be positively charged or negatively charged.

7 Claims, 5 Drawing Sheets

MALDI ANALYSIS USING MODIFIED MATRICES WITH AFFINITY GROUPS FOR NON-COVALENT BINDING WITH ANALYTES

CROSS-REFERENCE TO RELATED APPLICATIONS

This is a Continuation-In-Part application of U.S. application Ser. No. 10/755,986, filed Jan. 13, 2004 now U.S. Pat. No. 7,550,301, the disclosures of which are incorporated herein by reference in their entirety.

BACKGROUND OF THE INVENTION

1. Field of the Invention

This invention relates to methods and compounds to improve the desorption and ionization of analyte for mass spectrometry analysis. More specifically, this invention relates to the field of mass spectrometry, especially to the type of matrix-assisted laser desorption/ionization used to analyze macromolecules, such as proteins or biomolecules. Most specifically, this invention relates to the method of using photon energy absorbing molecules that can bind with analyte either temporarily or permanently to improve the desorption and ionization of analyte.

2. Background Information

This invention relates generally to methods and compounds for desorption and ionization of analytes for the purpose of subsequent scientific analysis by such methods, for example, as mass spectrometry (MS) or biosensors. Generally, analysis by mass spectrometry involves vaporization and ionization of a small sample of material, using a high energy source, such as a laser, including a laser beam. Certain molecules that can absorb the photon energy of laser beam can be added to the sample to aid the desorption and ionization of analytes. These photon absorbing molecules are called matrix. The material is vaporized from the surface of a probe tip into the gas or vapor phase by the laser beam, and, in the process, some of the individual molecules are ionized. The positively or negatively charged ionized molecules are then accelerated through a short high voltage field and let fly (drift) preferably into a high vacuum chamber, at the far end of which they strike a sensitive detector. In some mass spectrometry method, such as ion mobility spectrometry, atmosphere pressure instead of high vacuum is used. Since the time-of-flight is a function of the mass of the ionized molecule, the elapsed time between ionization and impact can be used to determine the molecule's mass which, in turn, can be used to identify the presence or absence of known molecules of specific mass. Besides using time-of-flight, other methods such as ion trap also can be used to detect the mass and intensity of ion. Matrix-assisted laser desorption/ionization (MALDI) mass spectrometry has become a very important tool of modern chemistry and biotechnology. It is highly desirable that certain analyte molecules can be selectively desorbed and ionized to reduce signal peak interference and improve detection sensitivity.

A patent search was conducted to examine the means for reducing signal peak interference and improved detection sensitivity for mass spectrometry. The following prior art patents were located in the course of the patent search, and are considered to be the references most pertinent to the invention.

The Nelson U.S. Pat. No. 6,093,541, issued on Jul. 25, 2000 illustrates a Mass spectrometer having a derivatized sample presentation apparatus;

The Nelson U.S. Pat. No. 6,316,266 issued on Nov. 13, 2001 illustrates a sample presentation apparatus for mass spectrometry;

The Hutchens U.S. Pat. No. 5,719,060 issued on Feb. 17, 1998 illustrates methods and apparatus for desorption and ionization of analytes for the purpose of subsequent scientific analysis by such methods;

The Giese; Roger U.S. Pat. No. 5,952,654 issued on Sep. 14, 1999 illustrates a field-release mass spectrometry methods of releasing and analyzing substrates such as DNA;

All the prior art patents examined involve modifying the sample presentation probe to selectively bind with certain analyte molecules and washing away the unbound analyte for improved detection. None of the prior art patents used modified matrix that can selectively form covalent or non-covalent interaction with certain analyte to improve their desorption and ionization. These methods involves heterogeneous binding, intensive washing, therefore are labor intensive, time consuming and may result in loss of analytes. They improve the detection of desired analyte indirectly by washing away interference molecules in the sample to decrease the noise and can not directly increase the desorption and ionization of desired analyte. The method in our invention is primarily directed towards direct increasing the desorption and ionization of desired analyte by forming a photon energy absorbing molecules-desired analyte complex for mass spectrometry analysis.

SUMMARY OF THE INVENTION

An object of the invention is to provide improved methods and materials for desorption and ionization of multiple or selected analytes into the gas (vapor) phase.

Another object is to provide means to selectively enhance the desorption/ionization of analyte molecules by using photon energy absorbing molecules that carry certain affinity groups.

A further object is to provide means to selectively enhance the desorption/ionization of analyte molecules by using photon energy absorbing molecules that carry certain reactive groups.

Other and further objects, features and advantages will be apparent and the invention will be more readily understood from a reading of the following specification and by reference to the accompanying drawings forming a part thereof, wherein the examples of the present preferred embodiments of the invention are given for the purposes of disclosure.

DESCRIPTION OF THE INVENTIONS AND THE PREFERRED EMBODIMENT

Figure 1:
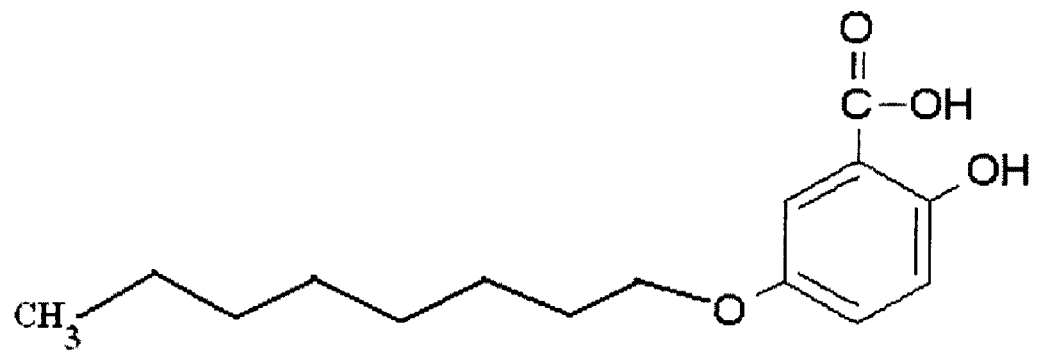
FIG. 1 shows an example of the selective affinity matrix.

Matrix for MALDI Mass (Matrix-assisted laser desorption/ionization mass spectrometry) is photon energy-absorbing molecules that can absorb energy from laser pulse and then push the analyte nearby into gas phase for mass analysis.

Currently, most matrix molecules are small organic molecule such as DHB (2,5-dihydroxy benzoic acid) and sinapinic acid, which cannot selectively desorb/ionize molecules from a complex mixture of analytes. These matrix molecules also can not selectively bind with analyte either covalently or non-covalently. To perform the mass spectrometry analysis, matrix is mixed with the sample containing analyte and then added onto the probe; the probe is then inserted into the MALDI mass spectrometer for the analysis.

In the current invention, photon energy absorbing molecules that can bind with certain analyte either temporarily or permanently are added to the sample solution to form a analyte-photon energy absorbing molecules complex during mixing and incubation; the resulting solution is then added onto the probe and the probe is inserted into the MALDI mass spectrometer for analysis. This kind of photon energy absorbing molecules are essentially matrix that can bind with analyte covalently or non-covalently, therefore are called binding matrix. In some embodiments, these binding matrix molecules comprise two parts conjugated together: a photon energy absorbing moiety and a binding moiety. The binding moiety can be reactive groups that can form covalent bond with target molecules. Alternatively, a carrier moiety or linker moiety is used to connect the photon energy absorbing moiety and the binding moiety. The carrier or linker can be a either small molecule or polymer or any other chemical entity can be used as a carrier/linker as long as it has multiple functional groups that allow direct or indirect conjugation of the photon energy absorbing moiety and the binding moiety. Appropriate natural or synthetic polymers include, but are not limited to, oligomers (such as peptides), linear or cross linked polymers (such as polylysine, polyacrylic acid, proteins) or highly branched macromolecules (such as dendrimers). The photon energy absorbing moiety can be matrix currently used or any other chemical entities that have strong photon energy absorbing capability. More than one photon energy absorbing unit and more than one binding unit can be incorporated in one unit of the binding matrix.

The photon energy absorbing molecules in the current invention include but not limited to the matrix molecules currently used in MALDI analysis such as cinnamamide, 2,5-dihydroxybenzoic acid and alpha-cyano-4-hydroxycinnamic acid. The photon energy absorbing molecules/moiety further include molecules that can strongly absorb the photon energy from IR, UV or visible light. Preferably these molecules should have a strong absorption for the light source used in the MALDI analysis. A skilled in the art can readily find many molecules and chemical moieties that have strong absorption for certain wavelength of photon. The chemical structures of strong photon energy absorbing molecules and chemical moieties are well known to the skilled in the art and can be readily found in the textbook of absorption spectrometry analysis. For example, aromatic compound and conjugated hetero cycles normally have strong UV absorption for UV light, especially when coupled with auxochrome. The chromophore and auxochrome in UV and visible light range are well known and the absorption band can be readily calculated from its chemical structure and adjusted by changing the chemical structure.

The binding could be either reactivity based covalent binding or affinity based non-covalent binding. Because matrix molecules absorb and transfer the energy to the molecules adjacent to them, selective binding of analytes to the matrix molecules can selectively desorb/ionize the analytes.

For non-covalent binding, the binding moiety are chemical entities with affinity groups having affinity for the analyte to be detected. The affinity group or groups can be any chemical or biological functionality with affinity for certain analytes. They include, but are not limited to, DNA, PNA (peptide nucleic acid), polynucleotides, antibody, antigen, aptamers, chelator, metals, lipophilic molecules, hydrophilic molecules, ionic molecules (such as acidic and basic molecules), dendrimer, polymers having affinity groups and other structures having specific affinity interactions with certain analytes. Through the binding between the affinity groups and the analytes, the non-covalent interaction between the matrix and the specific analytes will enable the matrix selectively desorb/ionize these analytes for mass analysis. This type of matrix is called affinity matrix. In some embodiments the photon-absorbing moiety is coupled directly to the affinity group. In other embodiments the photon-absorbing moiety is coupled to the affinity group though a linker/spacer. In some embodiments one affinity moiety is coupled with multiple photon-absorbing moieties.

The resulting mass detected could either be the mass of the analyte or the mass of analyte plus matrix based on the strength of the affinity. These novel matrix molecules could be used either alone or in combination with known matrix. This new method is useful in both single analyte detection and analytes pattern profiling such as protein pattern profiling for diagnosis, biomarker discovery and proteomic study. If multiple these kind of affinity matrix molecules are used for a sample containing multiple analytes, multiple analytes can be selectively detected simultaneously. Compared with other protein chip technologies and MALDI methods, this method provides a more sensitive and convenient solution.

For covalent binding, the binding moiety can be any chemical entities having certain reactive groups that can covalently couple to the analyte to be detected upon incubation, therefore these binding matrix molecules are indeed reactive matrix. The reactive groups include, but are not limited to anhydride, active ester, aldehyde, alkyl halide, acid chloride, isothiocyanate and other reactive groups that can react with functional group such as amine, hydroxyl, SH or other groups on the analyte molecules. Examples of active ester include but not limited to NHS ester, HOBt ester, HOAt ester, pentafluorophenyl ester and p-nitrophenyl ester. A skilled in the art can readily find more reactive groups from the textbook of organic synthesis. Upon mixing them together, the analyte molecules are covalently coupled with these reactive groups of the reactive matrix, and the masses detected are those of the adducts formed by the analyte molecules and the matrix. The desorption/ionization of certain molecules can thus be enhanced, and the mass spectra will exhibit a unique pattern of mass of derivatives which gives clues to structure of the molecules. These novel matrix molecules can be used either alone or in combination with known matrix.

It is well known that anhydride, active ester, aldehyde, alkyl halide, acid chloride can readily react with the target molecule's amine groups and hydroxyl, SH groups. One can easily find more reactive groups for certain functional groups on the target molecules in the text book of organic chemistry. The incubation can be done in either in organic or non-organic solvent depending on the solubility and reactivity of the reagents and analyte. In some embodiments the reactive group is conjugated directly to the photon-absorbing moiety. In other embodiments the reactive group is part of the photon-absorbing moiety. Yet in another embodiments the photon-absorbing moiety is coupled to the reactive group though a linker or spacer.

For example, a reactive matrix is a photon-absorbing molecule having a reactive group anhydride. In an analyte, there are molecules containing amine or —OH functionality, and molecules not containing amine functionality and —OH groups. When this reactive matrix is mixed with the analyte, its anhydride group reacts with amine or —OH to form covalent amide/ester bond, leaving molecules without amine/—OH group intact. If the molecule has 3 amine groups, some of them will react with one, two, and three matrix molecules respectively, and exhibit a series of masses of target molecule plus one, two and three photon-absorbing moiety in the spectra. By this method, the desorption/ionization of the molecule is selectively enhanced, and the mass pattern gives clues to its structural information.

Alternatively, pseudo-reactive matrix molecules can also be employed. A pseudo-matrix molecule is not a matrix by it self and can not absorb photon energy. It has a reactive group such as anhydride, aldehyde, alkyl halide, acid chloride, and other reactive groups that can react with functional group such as amine, hydroxyl, SH or other groups on the analyte molecules. When its reactive group reacts with a functional group and form a covalent bond, the resulting coupling product becomes capable of absorbing photon energy and performing desorption/ionization activity.

Further more, the photon energy absorbing molecules described above can have charged groups. After binding with analyte molecules, the formed product complex (either covalent or non-covalent) will carry the charged groups. These charged groups improve the ionization of the analyte complex and therefore improve the sensitivity of the MALDI analysis. The charged groups can be positively charged if MALDI is set to detect positive ion or be negatively charged in MALDI is set to detect negative ion. Preferably, the charged groups are strongly ionizable groups such as tertiary amine or quaternary amine for positive ions and phosphoric acid groups and sulphonic groups for negative ions. It is desirable that these charged groups are permanently charged, e.g. quaternary amine. In some embodiments the charged group is conjugated directly to the photon-absorbing moiety. In other embodiments the changed group is part of the photon-absorbing moiety. Yet in another embodiments the photon-absorbing moiety is coupled to the charged group though a linker or spacer.

Formula I shows an example of a charged affinity matrix used in some embodiments, which is essentially an affinity matrix described above having a charged group R. Here the affinity group is AB, which is an antibody having specific affinity to certain antigen. The charged group R is a functional group having a positive charge, such as a $(CH_3)_3N^+$—$CH_2$—O— group. This matrix is used for the detection of antigen specific to AB.

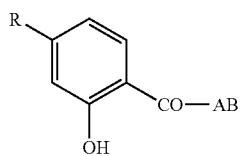

I

Formula II shows an example of a charged reactive matrix used in some embodiments, which is essentially a reactive matrix described above attached with a charged group R. Here the reactive group is X, such as an acid or active ester group or an anhydride group that can react with amine group/—OH group of the analyte readily. The charged group R is a functional group having a positive charge, such as a $(CH_3)_3N^+$—$CH_2$—O— group, or a guanidino group for positive ion MALDI, or a functional group having a negative charge, such as a —$CH_2OP(OH)_2OO^-$ group for negative ion MALDI.

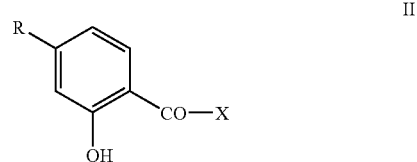

II

Because only the charged analyte can be detected in MALDI, therefore, aid in giving analyte charges can also enhance the sensitivity of MALDI. Charged affinity molecules that can specific bind with certain analyte would form a charged complex with the analyte molecule: charged affinity molecule plus analyte when mix them together. This charged complex can be easily detected and have high detection sensitivity since it is already charged. Therefore one can detect the analyte molecule easily by adding charged affinity molecule to the sample containing the analyte and detecting the complex formed by charged affinity molecule plus analyte in varieties of mass spectrometry methods. The high detecting sensitivity of the complex enables one to detect the specific analyte sensitively and selectively. Many markers that have unique patterns in mass spectrometry such as the bromine can be incorporated into the charged affinity molecule to aid the discrimination of the complex. In some embodiments the charged affinity molecules do not need to have the matrix effect. The mass detected is the mass of charged affinity molecule plus analyte. The formation of the detectable complex relies on the strong binding between the charged affinity molecule and the analyte. In one embodiment, Biotin is a small molecule that can bind with streptavidin tightly. $(CH_3)_3N^+$—$CH_2$—$NH_2$ is couple with biotin via amide bond to form a charged affinity molecule for streptavidin detection. Upon mixing them together, the detection of streptavidin will be enhanced due to the formed charged biotin+streptavidin complex. A non acidic matrix is preferred when using MALDI as the mass spectrometry method.

EXAMPLE 1

A DHB like molecule (photon absorbing moiety) is coupled with a lipophilic long alkyl chain (affinity moiety), therefore has affinity for lipophilic compounds (FIG. 1). This affinity matrix could selectively desorb/ionize lipophilic analyte in a mixture for MALDI mass analysis. Using this affinity matrix as matrix and standard MALDI analysis protocol (protocol available from Mass Spectrometry for Biotechnology; Gary Siuzdak, Academic Press 1996), a sample containing a mixture of dynorphin A-(1-11) and more lipophilic acetylated dynorphin A-(1-11) at 1:1 ratio gave 10 times higher peak of acetylated dynorphin A-(1-11) than the peak of less lipophilic dynorphin A-(1-11) while using DHB as matrix gave almost same peak height for two analytes. This enhanced signal of acetylated dynorphin A-(1-11) indicates the selective desorption/ionization capability of the lipophilic affinity matrix. The typical mixing and incubation time is several minutes. Longer incubation time can result in more complete binding. The affinity moiety is not limited to alkyl chain, for example, if the affinity moiety is biotin instead of the long alkyl chain, the resulting affinity matrix can be used to selectively desorb/ionize avidin or streptavidin.

EXAMPLE 2

Figure 2:
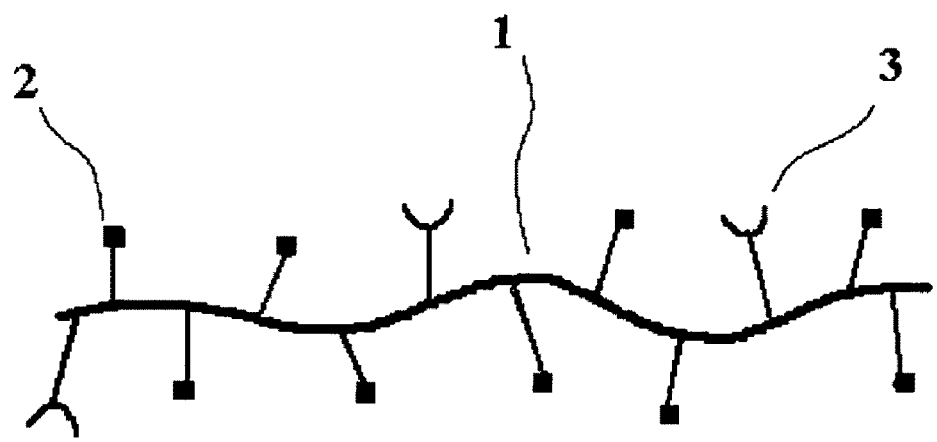
FIG. 2 shows another example of the polymer based selective affinity matrix.

FIG. 2 shows a polymer having both affinity groups and photon energy absorbing groups covalently coupled with it. The polymer 1 is polylysine (MW=20,000), the photon energy absorbing groups 2 are alpha-Cyano-4-hydroxycinnamic acid (CCA) molecules and the affinity groups 3 are antibodies. The CCA and antibodies are coupled to the side chains of polylysine via amide bonds. The preferred ratio of antibody to CCA is 1:5 to 1:20. This polymer can be used as a selective affinity matrix to selectively desorb/ionize the corresponding antigen in MALDI analysis. A further modification of this affinity matrix is that the affinity groups are covalently linked to the polymer back bone while the photon energy absorbing groups are bounded to the polymer by non-covalent interaction such as ion pairing or lipophilic interaction.

EXAMPLE 3

Figure 3:
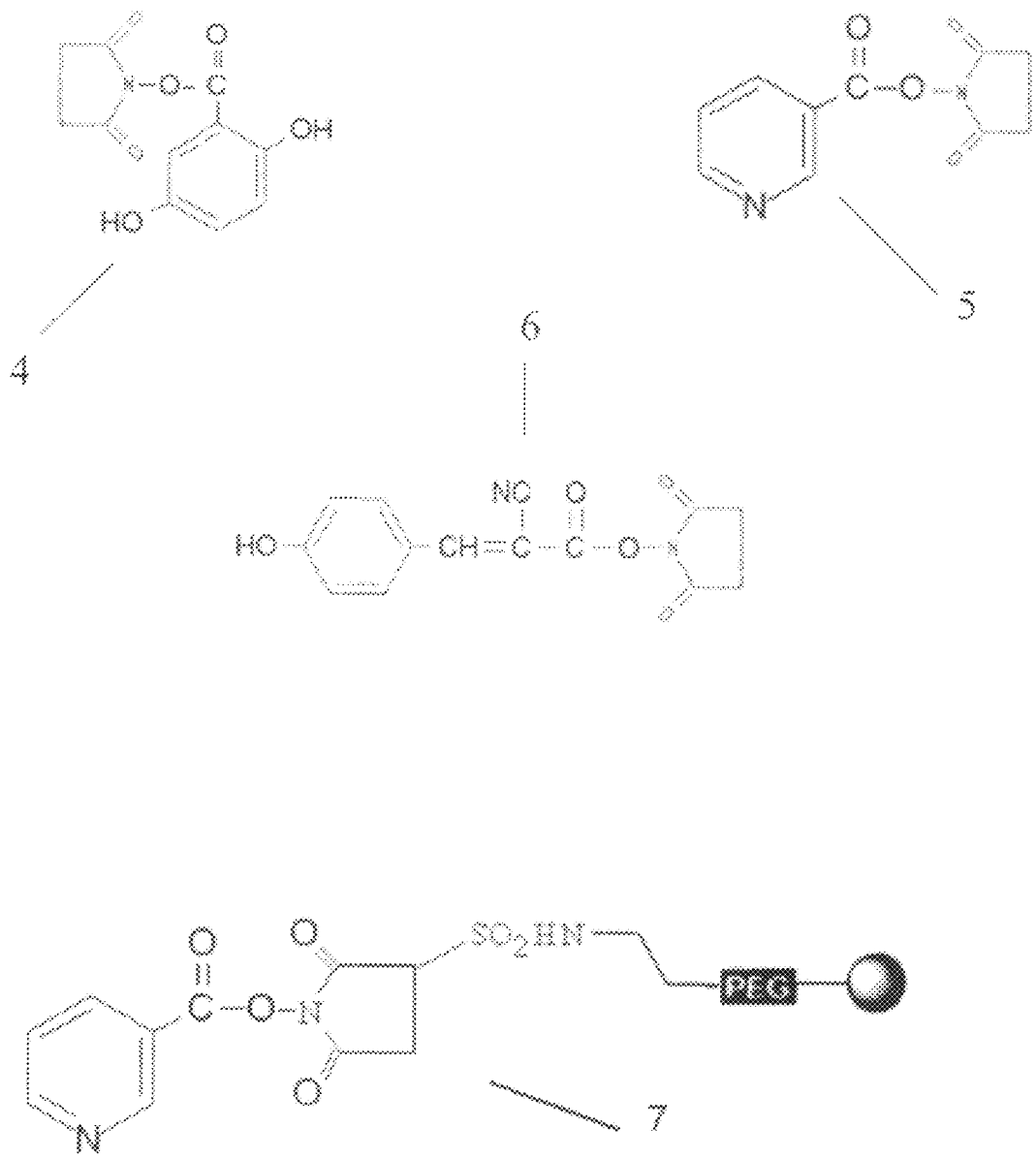
FIG. 3 shows examples of reactive matrix.

FIG. 3 shows the examples of several reactive matrix molecules: 2,5-Dihydroxybenzoic acid (DHB)-NHS ester, alpha-Cyano-4-hydroxycinnamic acid (CCA)-NHS ester and 3-Picolinic acid-NHS ester. The DHB-NHS ester 4, 3-Picolinic acid-NHS ester 5 and CCA-NHS ester 6 are active esters of known matrix DHB, CCA and 3-Picolinic acid respectively. They can react with the analyte molecules containing free amine groups upon mixing and incubation in sample solution. Preferred incubation time is 10~60 minutes. Using these reactive matrix molecules as matrix and standard MALDI analysis protocol, the analyte containing amine groups can be readily detected in MALDI analysis. Reactive matrix can also be immobilized on solid phase support such as the structure 7 in the figure, in structure 7, the 4, 3-Picolinic acid-NHS ester is immobilized on a PEG resin (Nova biochem), therefore allow easy purification of unreacted matrix.

EXAMPLE 4

Figure 4:
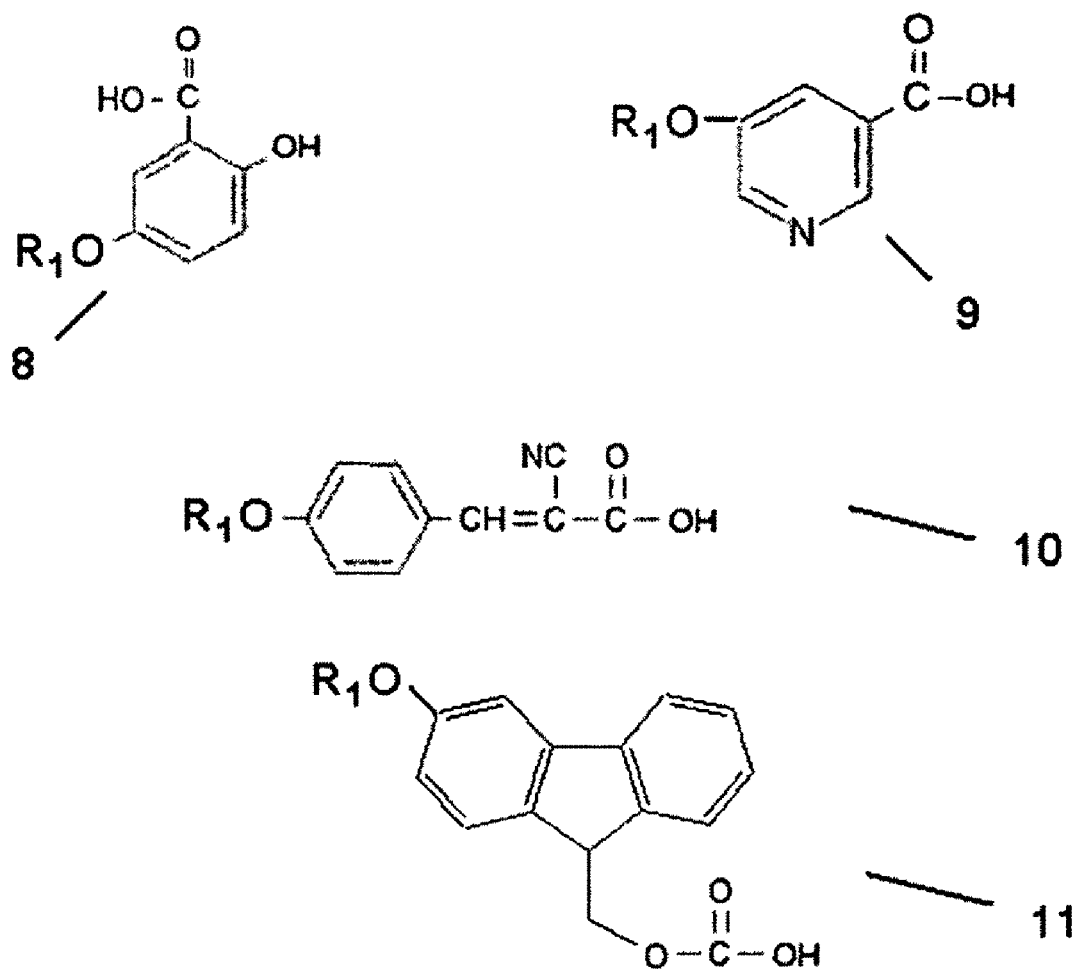
FIG. 4 shows examples of matrix carrying charged groups.

FIG. 4 shows the examples of several charged matrix molecules, R1 is a charged group such as $(CH_3)_3N^+$—$CH_2$— or $(CH_3)_2N$—$CH_2CH_2$—, R1 can also be other charged groups as long as it provide a strong ionizable groups which in clued but not limited to hetero cycles, alkyl amines and etc. 8, 9, 10 are 2,5-Dihydroxybenzoic acid (DHB), 3-Picolinic acid and alpha-Cyano-4-hydroxycinnamic acid (CCA) derivatives respectively. 11 is a Fmoc derivatives. Fmoc is s strong UV absorbing group. Further more, the photon absorbing moieties in FIG. 4 are not limited to the structure listed within, they can be any chemical groups as long as they have strong photon absorbing after they coupled with the analyte. These four charged matrix molecules can react with the analyte molecules containing free amine groups upon mixing and incubation in sample solution at the presence of coupling reagent. The solution can be either water based or organic solvent such as DMSO. Preferred incubation time is 10~60 minutes. Using these charged matrix molecules as matrix and standard MALDI analysis protocol; the analyte containing amine groups can be readily detected in MALDI analysis. In one embodiment, 5 mg of charged reactive matrix selected from 8, 9, 10 and 11 is mixed with 1 mg of avidin, an amine group containing protein in 0.1M PBS and 2 mg of EDC ((1-Ethyl-3-(3-dimethylaminopropyl) carbodiimide) for 30 min, next a drop of the mix is applied to the MALDI chip with a drop of 1% DHB aqueous solution, after drying, the MALDI analysis is performed, the peak shown has the molecular weight of avidin plus the matrix minus the leaving group during the coupling.

EXAMPLE 5

Figure 5:
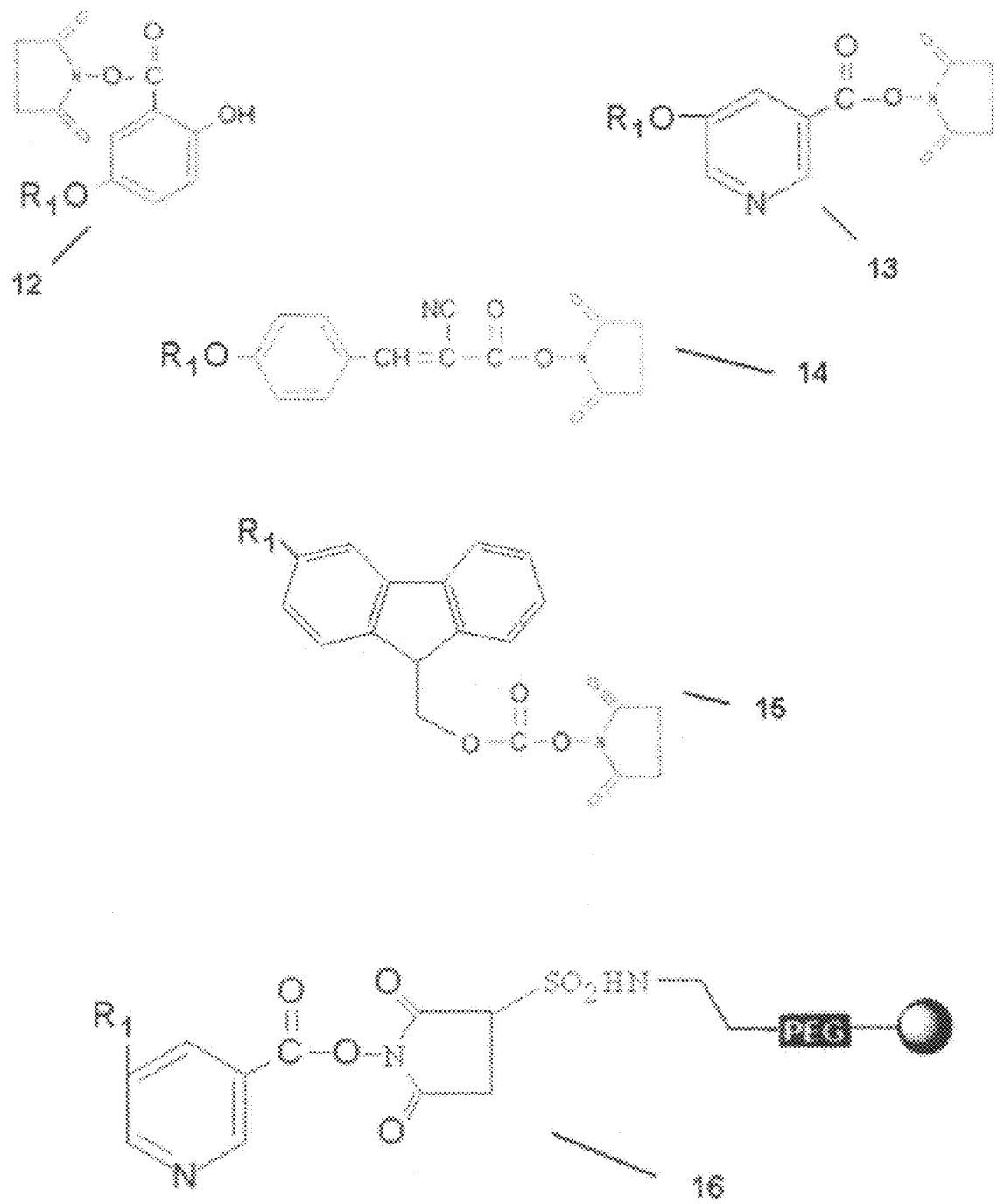
FIG. 5 shows examples of reactive matrix carrying charged groups in NHS ester form.

FIG. 5 shows the examples of several charged reactive matrix molecules, $R_1$ is a charged group such as $(CH_3)_3N^+$—$CH_2$— or $(CH_3)_2N$—$CH_2CH_2$—, $R_1$ can also be other charged groups as long as it provide a strong ionizable groups which in clued but not limited to hetero cycles, alkyl amines and etc. 12, 13 and 14 are charged derivatives of 2,5-Dihydroxybenzoic acid (DHB)-NHS ester, 3-Picolinic acid-NHS ester and alpha-Cyano-4-hydroxycinnamic acid (CCA)-NHS ester respectively. 15 is a Fmoc-NHS ester derivatives. Fmoc is s strong UV absorbing group. Further more, the photon absorbing moieties in FIG. 5 are not limited to the structure listed within, they can be any chemical groups as long as they have strong photon absorbing after they coupled with the analyte. These four charged reactive matrix molecules can react with the analyte molecules containing free amine groups upon mixing and incubation in sample solution. The solution can be either water based or organic solvent such as DMSO. Preferred incubation time is 10~60 minutes. Using these charged reactive matrix molecules as matrix and standard MALDI analysis protocol, the analyte containing amine groups can be readily detected in MALDI analysis. In one embodiment, 2 mg of charged reactive matrix selected from 12-15 is mixed with 1 mg of benzylamine in DMSO for 5 min, next a drop of the mix is applied to the MALDI chip with or without the addition of a drop of 5% DHB ethyl alcohol solution, after drying, the MALDI analysis is performed, the peak shown has the molecular weight of benzylamine plus reactive matrix minus the leaving group during the coupling (NHS group and $H_2O$). In structure 16, the 4, 3-Picolinic acid-NHS ester is immobilized on a PEG resin (Nova biochem), therefore allow easy purification of unreacted matrix. The resin can be removed from the coupling product before MALDI analysis. Similarly, the non-charged reactive matrix molecules in FIG. 3 can also be used instead.

EXAMPLE 6

Figure 6:
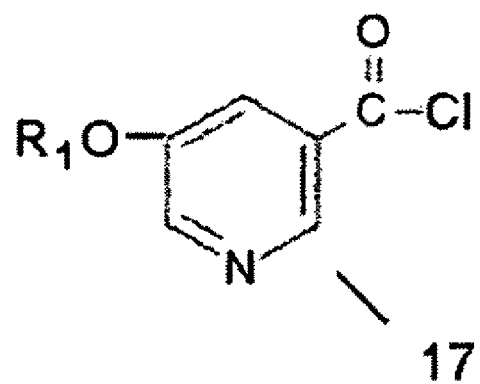
FIG. 6 shows examples of matrix carrying charged groups in acid chloride form.
Figure 6:
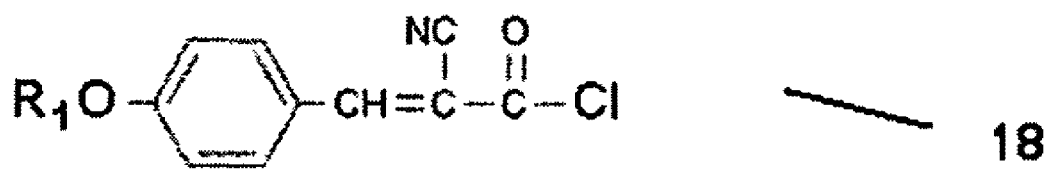
Figure 6:
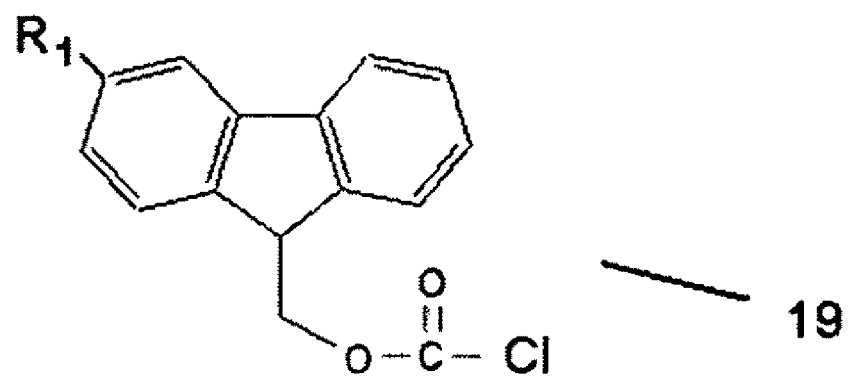

FIG. 6 shows the examples of several charged matrix molecules, $R_1$ is a charged group such as $(CH_3)_3N^+$— or $(CH_3)_2N$—$CH_2CH_2$—, $R_1$ can also be other charged groups as long as it provide a strong ionizable groups which in clued but not limited to hetero cycles, alkyl amines and etc. 17 and 18 are charged derivatives of 3-Picolinic acid chloride and alpha-Cyano-4-hydroxycinnamic acid (CCA) chloride respectively. 19 is a Fmoc chloride derivatives. These three charged matrix molecules can react with the analyte molecules containing free amine groups or —OH groups or —SH groups upon mixing and incubation in sample solution. The solution can be organic solvent such as acetone, DMF or DMSO. Preferred incubation time is 2~20 minutes. Using these charged matrix molecules as matrix and standard MALDI analysis protocol, the analyte containing amine groups/—OH group/—SH groups can be readily detected in MALDI analysis. In one embodiment, 2 mg of charged reactive matrix selected from 17~19 is mixed with 1 mg of cyclodextrin, an —OH group containing carbohydrate in DMSO for 30 min, next a drop of the mix is applied to the MALDI chip with/ without the addition of a drop of 5% DHB ethyl alcohol solution, after drying, the MALDI analysis is performed, the peak shown has the molecular weight of cyclodextrin plus the matrix minus the leaving group during the coupling.

EXAMPLE 7

The coupling product in example 4 is a charged matrix-avidin covalent complex, it is indeed an affinity matrix that can be used to detect its binding partner biotin. In one embodiment, 1 mg of purified charged affinity matrix-avidin is mixed with 10 ug of biotin in 100 ul 0.01 M PBS for 15 min, next a drop of the mix is applied to the MALDI chip with/without a drop of pH neutralized 1% CCA solution, after drying, the MALDI analysis is performed, the peak shown has the molecular weight of affinity matrix avidin plus biotin.

All patents and publications mentioned in this specification are indicative of the level of those skilled in the art to which the invention pertains. All patents and publications are herein incorporated by reference to the same extent as if each individual publication was specifically and individually indicated to be incorporated by reference. The inventions described above involve many well known chemistry, instruments, methods and skills. A skilled person can easily find these knowledge from text books such as the chemistry textbooks, scientific journal papers and other well known reference sources.

One skilled in the art will readily appreciate that the present invention is well adapted to carry out the objects and obtain the ends and advantages mentioned, as well as those inherent therein. The compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims.

What is claimed is:

1. A method for desorbing analyte molecules from a sample presenting surface, comprising:
   providing photon energy absorbing molecules having an affinity group which can form non-covalent bond with analyte;
   mixing and incubating said photon energy absorbing molecules with a sample solution containing said analytes to form a non-covalent complex between said analyte and said photon energy absorbing molecule; and
   exposing said complex deposited on the sample presenting surface, to a laser source to desorb the analyte or the complex from said surface.

2. A method for desorbing an analyte molecule from a sample presenting surface for MALDI mass spectrometry analysis, comprising:
   providing a soluble photon energy absorbing molecule having an affinity group that can bind with said analyte molecule via a non-covalent bond;
   mixing and incubating said photon energy absorbing molecule with a sample containing said analyte to form a solution containing a noncovalently bound complex between said analyte and said photon energy absorbing molecule;
   depositing the solution containing the bound complex on the sample presenting surface, and
   exposing said complex deposited on the sample presenting surface to a laser source to desorb the analyte or the complex from the surface for MALDI analysis.

3. The method according to claim 2, wherein the photon energy absorbing molecule has a charged group.

4. The method according to claim 3, wherein the charged group is a positively charged group.

5. The method according to claim 3, wherein the charged group is a negatively charged group.

6. The method according to claim 2, wherein the affinity group is selected from antibody, antigen, aptamer, polynucleotides, chelators, metals, lipophilic molecules, hydrophilic molecules, and ionic molecules.

7. The method according to claim 2, wherein the photon energy absorbing molecule contains a photon energy absorbing moiety selected from cinnamamide, 2,5-dihydroxybenzoic acid, picolinic acid and cinnamic acid.

* * * * *